(12) United States Patent
Economides et al.

(10) Patent No.: US 6,846,908 B2
(45) Date of Patent: Jan. 25, 2005

(54) DCR-5 BONE AFFECTING LIGAND

(75) Inventors: Aris N. Economides, Tarrytown, NY (US); Neil Stahl, Carmel, NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 0 days.

(21) Appl. No.: 10/662,756

(22) Filed: Sep. 15, 2003

(65) Prior Publication Data

US 2004/0106134 A1 Jun. 3, 2004

Related U.S. Application Data

(62) Division of application No. 09/762,960, filed as application No. PCT/US99/17979 on Aug. 12, 1999, now Pat. No. 6,660,499.
(60) Provisional application No. 60/097,296, filed on Aug. 20, 1998.

(51) Int. Cl.[7] .................. C07K 14/00; C07K 16/00; C12P 21/06; C12P 15/74; C12P 5/02
(52) U.S. Cl. ............... 530/350; 530/387.9; 530/388.1; 435/69.1; 435/320.1; 435/325; 514/2
(58) Field of Search .................. 530/350, 387.9, 530/388.1; 435/69.1, 320.1, 325; 514/2

(56) References Cited

FOREIGN PATENT DOCUMENTS

| WO | WO98/33918 | 8/1998 |
|---|---|---|
| WO | WO99/03996 | 1/1999 |
| WO | WO99/06552 | 2/1999 |
| WO | WO00/11163 | 3/2000 |

OTHER PUBLICATIONS

Harlow, E., and Lane, D. Antibodies, 1989.*
Ashkenazi, A., and Chamow, S. Current Opinion in Immunology, 1997, vol. 9, pp. 195–200.*
Nature, Bouwmeester, et al., 1996, "Cerebrus is a head–inducing secreted factor expressed in the anterior endoderm of Spemann's organizer," 382:595–601.
Science, Lamb, T. M., et al., 1993, "Neural Induction by the Secreted Polypeptide Noggin," 262:713–718.
Cell, Smith, W. C., et al., 1992, "Expression Cloning of noggin, a New Dorsalizing Factor Localized to the Spemann Organizer in Xenopus Embryos," 70:829–840.
Nature, Smith, W. C., et al., 1993, "Secreted noggin protein mimics the Spemann organizer in dorsalizing Xenopus mesoderm," 361:547–549.
Cell, Zimmerman, L. B., et al., 1996, "The Spemann Organizer Signal noggin Binds and Inactivates Bone Morphogenic Protein 4," 86:599–606.
Cell, Piccolo, S., et al., 1996, "Dorsoventral Patterning in Xenopus: Inhibition of Ventral Signals by Direct Binding of Chordin to BMP–4," 86:589–598.
Nature, Sasai, Y. et al., 1995, "Regulation of neural induction by the Chd and the Bmp–4 antagonistic patterning signals in Xenopus," 376:333–336.
Cell, Sasai, Y., et al., 1994, "Xenopus chordin: A Novel Dorsalizing Factor Activated by Organizer–Specific Homeobox Genes," 79:779–790.
Oncogene, Enomoto, et al., 1994, "Identification of human DAN gene, mapping to the putative neuroblastoma tumor suppressor locus," 9:2785–2791.
JPN. J. Cancer Res., Ozaki, et al., 1996, "Cloning of Mouse DAN cDNA and its Down–regulation in Transformed Cells," 87:58–61.
Mol Cell, Hsu, et al., 1998, "The Xenopus Dorsalizing Factor Gremlin Identifies a Novel Family of Secreted Proteins that Antagonize BMP Activities," 1:673–683.
Dev Growth Differ, Minabe–Saegusa, C. et al., 1998, "Sequence and expression of a novel mouse gene PRDC (protein related to DAN and cerebrus) identified by a gene trap approach," 40:343–353.
Gene, Holler, T.P., et al., 1993, "HIV1 integrase expressed in *Escherichia coli* from a synthetic gene," 136:323–328.
Gene, Martin, S.L., et al., 1995, "Total synthesis and expression in *Escherichia coli* of a gene encoding human tropoelastin," 154:159–166.
Science, Davis, S., et al., 1994, "Ligands for EPH–Related Receptor Tyrosine Kinases That Require Membrane Attachment or Clustering for Activity," 266:816–819.

* cited by examiner

Primary Examiner—Janet Andres
(74) Attorney, Agent, or Firm—Valeta Gregg, Esq.

(57) ABSTRACT

DCR5, a protein related to DAN (Differential-screening-selected gene Aberrative in Neuroblastoma) and related nucleic acids are provided. Included are natural DCR5 homologs from several species and proteins comprising a DCR5 domain having specific activity, particularly the ability to antagonize a bone morphogenetic protein. The proteins may be produced recombinantly from transformed host cells with the subject nucleic acids. Also provided are isolated hybridization probes and primers capable of specifically hybridizing with the disclosed genes, specific binding agents and methods of making and using the subject compositions.

6 Claims, No Drawings

DCR-5 BONE AFFECTING LIGAND

CROSS-REFERENCE TO RELATED APPLICATIONS

This application is a divisional of U.S. application Ser. No. 09/762,960, filed Feb. 14, 2001, now U.S. Pat. No. 6,660,499, which is a U.S. National Stage Application of International Application No. PCT/US99/17979, filed Aug. 12, 1999, which claims the benefit of U.S. Provisional Application No. 60/097,296, filed Aug. 20, 1998, now abandoned, the disclosures of which are incorporated herein by reference in their entireties.

REFERENCE TO SEQUENCE LISTING

This application refers to sequences listed in a Sequence Listing attached hereto, which is considered to be part of the disclosure of the invention.

FIELD OF THE INVENTION

The field of this invention is proteins which regulate cell function, and in particular, antagonize bone morphogenetic proteins.

RELATED ART

Bouwmeester, et al. (1996) Nature 382: 595–601 describe the cloning of *Xenopus cerberus* gene; Lamb, T. M., et al. (1993) Science 262: 713–718; Smith, W. C., et al. (1992) Cell 70: 829–840; Smith, W. C., et al. (1993) Nature 361: 547–549; and Zimmerman, L. B., et al. (1996) Cell 86: 599–606 describe the isolation and function of the Noggin protein. Piccolo, S., et al. (1996) Cell 86: 589–598; Sasai, Y., et al. (1995) Nature 376: 333–336; and Sasai, Y., et al. (1994) Cell 79: 779–790 relate to the chordin protein. Enomoto et al. (1994) Oncogene 9: 2785–2791 and Ozaki, et al. (1996) Jpn. J. Cancer Res. 87: 58–61 describe human and murine homologs of the DAN gene. Hsu, et al. (1998) Mol Cell 1:673–683 describing Gremlin from a variety of species, including human; Minabe-Saegusa, C., et al. (1998) Dev Growth Differ 40:343–353 which describes mouse PRDC.

SUMMARY OF THE INVENTION

The invention provides methods and compositions relating to DCR5, a protein related to Gremlin, DAN (Differential-screening-selected gene Aberrative in Neuroblastoma) and Cerberus, and related nucleic acids. Included are natural DCR5 homologs from different species, as well as proteins comprising a DCR5 domain and having DCR5-specific activity, particularly the ability to antagonize a bone morphogenetic protein. The proteins may be produced recombinantly from transformed host cells with the subject nucleic acids. The invention provides isolated hybridization probes and primers capable of specifically hybridizing with the disclosed genes, specific binding agents such as specific antibodies, and methods of making and using the subject compositions in diagnosis (e.g., genetic hybridization screens for DCR5 transcripts), therapy (e.g., gene therapy to modulate DCR5 gene expression) and in the biopharmaceutical industry (e.g., reagents for screening chemical libraries for lead pharmacological agents).

Preferred applications of the subject DCR5 proteins include modifying the physiology of a cell comprising an extracellular surface by contacting the cell or medium surrounding the cell with an exogenous DCR5 protein under conditions whereby the added protein specifically interacts with a component of the medium and/or the extracellular surface to effect a change in the physiology of the cell. Also preferred are methods for screening for biologically active agents, which methods involve incubating a DCR5 protein in the presence of an extracellular DCR5 protein-specific binding target and a candidate agent, under conditions whereby, but for the presence of the agent, the protein specifically binds the binding target at a reference affinity; detecting the binding affinity of the protein to the binding target to determine an agent-biased affinity, wherein a difference between the agent-biased affinity and the reference affinity indicates that the agent modulates the binding of the protein to the binding target.

Another preferred embodiment of the invention is a method of treatment of a human or animal body by administering a therapeutic dosage of a human DCR5 polypeptide wherein the treatment is regulation of cartilage and bone growth.

An additional preferred embodiment of the invention is a ligandbody which comprises human DCR5 fused to an immunoglobulin constant region, wherein the immunoglobulin constant region is the Fc portion of human IgG1.

In a preferred embodiment, a ligandbody may be used in a method of treatment of the human or animal body, or in a method of diagnosis.

DETAILED DESCRIPTION OF THE INVENTION

The invention provides DCR5 proteins which include natural DCR5 proteins and recombinant proteins comprising a DCR5 amino acid sequence, or a functional DCR5 protein domain thereof having an assay-discernable DCR5-specific activity. Accordingly, the proteins may be deletion mutants of the disclosed natural DCR5 proteins and may be provided as fusion products, e.g., with non-DCR5 polypeptides. The subject DCR5 protein domains have DCR5-specific activity or function and are functionally distinct from each other and from DAN, cerberus, Gremlin and Noggin homologs. Such domains include at least 6 and preferably at least 8 consecutive residues of a natural DCR5 protein (See DAN sequence reported by Enomoto, et al. (1994) Oncogene 9: 2785–2791). Preferred DCR5 proteins comprise a DCR5 sequence conserved across species.

The DCR5 proteins described herein are structurally and functionally related to DAN and Cerberus in that they are extracellularly active as antagonists of certain morphogenetic proteins such as BMPs. DCR5-specific activity or function may be determined by convenient in vitro, cell-based, or in vivo assays—e.g., in vitro binding assays, cell culture assays, in animals (e.g., immune response, gene therapy, transgenics, etc.), etc. Binding assays encompass any assay where the specific molecular interaction of a DCR5 protein with a binding target is evaluated. The binding target may be a natural binding target such as a TGFβ protein, a morphogenetic protein, preferably a bone morphogenetic protein such as BMP2 or BMP4, a chaperone, or other regulator that directly modulates DCR5 activity or its localization; or non-natural binding target such as a specific immune protein such as an antibody, or a DCR5 specific agent such as those identified in assays described below. Generally, binding specificity is assayed by bioassay (e.g., the ability to induce neuronal tissue from injected embryonic ectoderm), TGFβ protein binding equilibrium constants (usually at least about $10^7$ $M^{-1}$, preferably at least about $10^8$ $M^{-1}$, more preferably at least about $10^9$ $M^{-1}$), by the ability of the subject protein to function as negative mutants in DCR5-expressing cells, to elicit DCR5-specific antibody in a heterologous host (e.g., a rodent or rabbit), etc.

The claimed proteins may be isolated or pure—an "isolated" protein is one that is no longer accompanied by some of the material with which it is associated in its natural state, and that preferably constitutes at least about 0.5%, and more preferably at least about 5% by weight of the total protein in a given sample; a "pure" protein constitutes at least about 90%, and preferably at least about 99% by weight of the total protein in a given sample. The subject proteins and protein domains may be synthesized, produced by recombinant technology, or purified from cells. A wide variety of molecular and biochemical methods are available for biochemical synthesis, molecular expression and purification of the subject compositions, see e.g., Molecular Cloning, A Laboratory Manual (Sambrook, et al., Cold Spring Harbor Laboratory), Current Protocols in Molecular Biology (Eds. Ausubel, et al., Greene Publ. Assoc., Wiley-Interscience, NY).

The subject proteins find a wide variety of uses including use as immunogens, targets in screening assays, bioactive reagents for modulating cell growth, differentiation and/or function, etc. For example, the invention provides methods for modifying the physiology of a cell comprising an extracellular surface by contacting the cell or medium surrounding the cell with an exogenous DCR5 protein under conditions whereby the added protein specifically interacts with a component of the medium and/or the extracellular surface to effect a change in the physiology of the cell. According to these methods, the extracellular surface includes plasma membrane-associated receptors; the exogenous DCR5 refers to a protein not made by the cell or, if so, expressed at non-natural levels, times or physiologic locales; and suitable media include in vitro culture media and physiological fluids such as blood, synovial fluid, etc. Effective administrations of subject proteins can be used to reduce undesirable (e.g., ectopic) bone formation, inhibit the growth of cells that require a morphogenetic protein (e.g., BMP-dependent neuroblastomas and gliomas), alter morphogen-dependent cell fate/differentiation in culture, such as with cells for transplantation or infusion, etc. The proteins may be introduced, expressed, or repressed in specific populations of cells by any convenient way such as microinjection, promoter-specific expression of recombinant enzyme, targeted delivery of lipid vesicles, etc.

The invention provides natural and non-natural DCR5-specific binding agents, methods of identifying and making such agents, and their use in diagnosis, therapy and pharmaceutical development. DCR5-specific binding agents include DCR5-specific ligands such as BMPs, and receptors, such as somatically recombined protein receptors like specific antibodies or T-cell antigen receptors (See, e.g., Harlow and Lane (1988) Antibodies, A Laboratory Manual, Cold Spring Harbor Laboratory) and also includes other natural binding agents identified with assays such as one-, two- and three-hybrid screens, and non-natural binding agents identified in screens of chemical libraries such as described below. Agents of particular interest modulate DCR5 function.

The invention provides DCR5 nucleic acids, which find a wide variety of applications including use as translatable transcripts, hybridization probes, PCR primers, diagnostic nucleic acids, etc., as well as use in detecting the presence of DCR5 genes and gene transcripts and in detecting or amplifying nucleic acids encoding additional DCR5 homologs and structural analogs.

The subject nucleic acids are of synthetic/non-natural sequences and/or are isolated, i.e., no longer accompanied by some of the material with which it is associated in its natural state, preferably constituting at least about 0.5%, more preferably at least about 5% by weight of total nucleic acid present in a given fraction, and usually recombinant, meaning they comprise a non-natural sequence or a natural sequence joined to nucleotide(s) other than that which it is joined to on a natural chromosome. Nucleic acids comprising the nucleotide sequence of SEQ ID NO: 11 or fragments thereof, contain such sequence or fragment at a terminus, immediately flanked by a sequence other than that to which it is joined on a natural chromosome, or flanked by a native flanking region fewer than 10 kb, preferably fewer than 2 kb, which is immediately flanked by a sequence other than that to which it is joined on a natural chromosome. While the nucleic acids are usually RNA or DNA, it is often advantageous to use nucleic acids comprising other bases or nucleotide analogs to provide modified stability, etc.

The amino acid sequences of the disclosed DCR5 proteins are used to back translate DCR5 protein-encoding nucleic acids optimized for selected expression systems (Holler, et al. (1993) Gene 136: 323–328; Martin, et al. (1995) Gene 154: 150–166) or used to generate degenerate oligonucleotide primers and probes for use in the isolation of natural DCR5 encoding nucleic acid sequences ("GCG" software, Genetics Computer Group, Inc., Madison, Wis.). DCR5 encoding nucleic acids may be part of expression vectors and may be incorporated into recombinant host cells, e.g., for expression and screening, for transgenic animals, for functional studies such as the efficacy of candidate drugs for disease associated with DCR5 mediated signal transduction, etc. Expression systems are selected and/or tailored to effect DCR5 protein structural and functional variants through alternative post-translational processing.

The invention also provides for nucleic acid hybridization probes and replication/amplification primers having a DCR5 cDNA specific sequence and sufficient to effect specific hybridization with SEQ ID NO: 11. Demonstrating specific hybridization generally requires stringent conditions, for example, hybridizing in a buffer comprising 30% formamide in 5×SSPE (0.18 M NaCl, 0.01 M NaPO$_4$, pH7.7, 0.001 M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C. DCR5 cDNA homologs can also be distinguished from other protein using alignment algorithms, such as BLASTX (Altschul, et al. (1990) Basic Local Alignment Search Tool, J. Mol. Biol. 215: 403–410).

DCR5 hybridization probes find use in identifying wild-type and mutant alleles in clinical and laboratory samples. Mutant alleles are used to generate allele-specific oligonucleotide (ASO) probes for high-throughput clinical diagnoses. DCR5 nucleic acids are also used to modulate cellular expression or intracellular concentration or availability of active DCR5. DCR5 inhibitory nucleic acids are typically antisense—single stranded sequences comprising complements of the disclosed natural DCR5 coding sequences. Antisense modulation of the expression of a given DCR5 protein may employ antisense nucleic acids operably linked to gene regulatory sequences. Cells are transfected with a vector comprising a DCR5 sequence with a promoter sequence oriented such that transcription of the gene yields an antisense transcript capable of binding to endogenous DCR5 encoding mRNA. Transcription of the antisense nucleic acid may be constitutive or inducible and the vector may provide for stable extrachromosomal maintenance or integration. Alternatively, single-stranded antisense nucleic acids that bind to genomic DNA or mRNA encoding a given DCR5 protein may be administered to the target cell, in or temporarily isolated from a host, at a concentration that results in a substantial reduction in expression of the targeted protein. An enhancement in DCR5 expression is effected by introducing into the targeted cell type DCR5 nucleic acids which increase the functional expression of the corresponding gene products. Such nucleic acids may be DCR5 expression vectors, vectors which up-regulate the functional expression of an endogenous allele, or replacement vectors for targeted correction of mutant alleles. Techniques for introducing the nucleic acids into viable cells are known in the art and include retroviral-based transfection, viral coat protein-liposome mediated transfection, etc.

The invention provides efficient methods of identifying agents, compounds or lead compounds for agents active at the level of DCR5 modulatable cellular function. Generally, these screening methods involve assaying for compounds which modulate DCR5 interaction with a natural DCR5 binding target. A wide variety of assays for binding agents are provided including protein-protein binding assays, immunoassays, cell based assays, etc. Preferred methods are amenable to automated, cost-effective high throughput screening of chemical libraries for lead compounds.

In vitro binding assays employ a mixture of components including a DCR5 protein, which may be part of a fusion product with another peptide or polypeptide, e.g., a tag for detection or anchoring, etc. The assay mixtures comprise a natural DCR5 binding target, e.g., a TGFβ protein such as a BMP. While native binding targets may be used, it is frequently preferred to use portions thereof as long as the portion provides binding affinity and avidity to the subject DCR5 conveniently measurable in the assay. The assay mixture also comprises a candidate pharmacological agent. Candidate agents encompass numerous chemical classes, though typically they are organic compounds, preferably small organic compounds, and are obtained from a wide variety of sources including libraries of synthetic or natural compounds. A variety of other reagents such as salts, buffers, neutral proteins, e.g., albumin, detergents, protease inhibitors, nuclease inhibitors, antimicrobial agents, etc., may also be included. The mixture components can be added in any order that provides for the requisite bindings and incubations may be performed at any temperature which facilitates optimal binding. The mixture is incubated under conditions whereby, but for the presence of the candidate pharmacological agent, the DCR5 specifically binds the cellular binding target, portion or analog with a reference binding affinity. Incubation periods are chosen for optimal binding but are also minimized to facilitate rapid, high throughput screening.

After incubation, the agent-biased binding between the DCR5 and one or more binding targets is detected by any convenient way. For cell-free binding type assays, a separation step is often used to separate bound from unbound components. Separation may be effected by precipitation, immobilization, etc., followed by washing by, e.g., membrane filtration or gel chromatography. For cell-free binding assays, one of the components usually comprises or is coupled to a label. The label may provide for direct detection as radioactivity, luminescence, optical or electron density, etc., or indirect detection such as an epitope tag, an enzyme, etc. A variety of methods may be used to detect the label depending on the nature of the label and other assay components, e.g., through optical or electron density, radiative emissions, non-radiative energy transfers, or indirectly detected with antibody conjugates, etc. A difference in the binding affinity of the DCR5 protein to the target in the absence of the agent as compared with the binding affinity in the presence of the agent indicates that the agent modulates the binding of the DCR5 protein to the corresponding binding target. A difference, as used herein, is statistically significant and preferably represents at least a 50%, more preferably at least a 90% difference.

The invention provides for a method for modifying the physiology of a cell comprising an extracellular surface in contact with a medium, said method comprising the step of contacting said medium with an exogenous DCR5 protein under conditions whereby said protein specifically interacts with at least one of a component of said medium and said extracellular surface to effect a change in the physiology of said cell.

The invention further provides for a method for screening for biologically active agents, said method comprising the steps of a) incubating a DCR5 protein in the presence of an extracellular DCR5 protein specific binding target and a candidate agent, under conditions whereby, but for the presence of said agent, said protein specifically binds said binding target at a reference affinity; b) detecting the binding affinity of said protein to said binding target to determine an agent-biased affinity, wherein a difference between the agent-biased affinity and the reference affinity indicates that said agent modulates the binding of said protein to said binding target.

The invention also provides for the production of ligandbodies. Ligandbodies are comprised of a ligand polypeptide coupled to the Fc domain of IgG and are able to dimerize (see for example Davis, et al., 1994, Science 266:816–819). Ligandbodies have the advantage of exhibiting enhanced pharmacokinetic properties. Thus, DCR5 ligandbodies may be useful in therapeutic applications where enhanced pharmacokinetic properties of DCR5 is desirable.

One embodiment of the invention is an isolated DCR5 protein comprising the amino acid sequence as set forth in SEQ ID NO: 12 or a fragment thereof having DCR5-specific activity.

Another embodiment of the invention is a recombinant nucleic acid encoding DCR5 protein comprising the amino acid sequence as set forth in SEQ ID NO: 12 or a fragment thereof having DCR5-specific activity.

Still another embodiment is an isolated nucleic acid comprising a nucleotide sequence as set forth in SEQ ID NO: 11 or a fragment thereof having at least 18 consecutive bases of SEQ ID NO: 11 and sufficient to specifically hybridize with a nucleic acid having the sequence of SEQ ID NO: 11 in the presence of natural DAN and cerberus cDNA.

Another preferred embodiment of the invention is a method of treatment of a human or animal body by administering a therapeutic dosage of a human DCR5 polypeptide as wherein the treatment is regulation of cartilage and bone growth.

The present invention also provides for antibodies to the DCR5 protein described herein which are useful for detection of the protein in, for example, diagnostic applications. For preparation of monoclonal antibodies directed toward this DCR5 protein, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in "Monoclonal Antibodies and Cancer Therapy," Alan R. Liss, Inc. pp. 77–96) and the like are within the scope of the present invention.

The monoclonal antibodies for diagnostic or therapeutic use may be human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80:7308–7312; Kozbor et al., 1983, Immunology Today 4:72–79; Olsson et al., 1982, Meth. Enzymol. 92:3–16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

Various procedures known in the art may be used for the production of polyclonal antibodies to epitopes of the DCR5 protein described herein. For the production of antibody, various host animals can be immunized by injection with the DCR5 protein, or a fragment or derivative thereof, including but not limited to rabbits, mice and rats. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, polypeptides, oil emulsions, keyhole limpet hemocyanins, dinitrophenol, and potentially useful human adjuvants such as BCG (Bacille Calmette-Guerin) and *Corynebacterium parvum*.

A molecular clone of an antibody to a selected DCR5 protein epitope can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

The present invention provides for antibody molecules as well as fragments of such antibody molecules. Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent. Antibody molecules may be purified by known techniques, e.g., immunoabsorption or immunoaffinity chromatography, chromatographic methods such as HPLC (high performance liquid chromatography), or a combination thereof.

The invention further provides for a method of using a DCR5 protein or fragment thereof as an antagonist of the activity of a bone morphogenetic protein (BMP), either alone, or in combination with other factors, including DAN, Cerberus, b57 or von Willebrand factor to regulate or modulate the activity of a BMP.

The following examples are offered by way of illustration and not by way of limitation.

EXAMPLES

Example 1

Cloning of Human DCR5

Searching of the nucleotide database at NCBI using the human Gremlin (hGRE) nucleotide sequence as a query, pooled out an entry encoding for a murine protein termed PRDC [Minabe-Saegusa, 1998], for "Protein Related to DAN and Cerberus". PCR was used to clone the murine PRDC from genomic DNA as well as several murine cDNA sources (brain, smooth muscle, skeletal muscle, liver, embryonic day 15 embryo, embryonic day 17 embryo). The open reading frame (ORF) encoding murine PRDC lies on a single exon. We extrapolated that if the PRDC ORF lies on a single exon, then its human homolog, which was designated human DCR5 (for human DAN/Cerberus related gene number 5), should also lie on a single exon, allowing the use of human genomic DNA in screening for the complete ORF of this gene. Furthermore, we used the PRDC ORF as a probe to investigate the expression of the putative human DCR5 on Multiple Human Tissue Northern blots (Clontech), and it appeared to be expressed in brain, placenta, liver, skeletal muscle, small intestine, colon (mucosal lining), stomach, colon (muscle), small intestine (muscle), bladder (muscle), stomach (muscle), and prostate (muscle), thus pointing to several sources of cDNA that could be used to clone the hDCR5 cDNA.

The peptide sequence of PRDC was aligned to all the known members of the DAN/Cerberus (DAN/CER) family and regions that are highly conserved were determined. One of the most striking features of the proteins belonging to the DAN/CER family is a conserved pattern of cysteines (Cys). Four different amino acid sequences that contained some of these Cys residues were chosen to design four degenerate oligonucleotide primers with the following sequences:

```
(a) DCR5.d1-5'
MGN AAR TAY YTN AAR WSN GAY TGG TGY          (SEQ ID NO: 1)
(Arg) Lys Tyr (Leu) Lys (Ser) Asp Trp Cys>
65                                       73

(b) DCR5.d2-5'
CAR ACN GTN WSN GAR GAR GGN TGY              (SEQ ID NO: 2)
Gln Thr Val (Ser) Glu Glu Gly Cys>
80                                  87

(c) DCR5.d3-3'
NGG NGG RTC NAR NCC NGG RCA                  (SEQ ID NO: 3)
<Pro Pro Asp (Leu) Gly Pro Cys
143                              137

(d) DCR5.d4-3'
NAR RTT NAC NSW CAT RCA NCK RCA              (SEQ ID NO: 4)
<(Leu) Asn Val (Ser) Met Cys (Arg) Cys
162                                    155
```

Key: Degenerate bases are indicated using IUPAC nomenclature. Amino acids in parentheses indicate the amino acid present at that position in murine PRDC. Numbers in italics indicate the amino acid number in the sequence of PRDC protein (starting with the initiating Methionine as amino acid number 1). The direction of the amino acid sequence is reversed for primers DCR5.d3-3' (SEQ ID NO: 3) and DCR5.d4-3' (SEQ ID NO: 4) as indicated by arrows (<).

We employed primers DCR5.d1-5' (SEQ ID NO: 1) and DCR5.d4-3' (SEQ ID NO: 4) (i.e. the outermost primers in the sequence of PRDC) to set up PCR using human genomic DNA as the template, using standard PCR methodology. The products of these reactions were used as a template for a second set of PCR reactions using primers DCR5.d2-5' (SEQ ID NO: 2) and DCR5.d3-3' (SEQ ID NO: 3). This second PCR reactions amplified a DNA fragment of approximately 200 base pairs, which was close to the size expected according to the PRDC sequence. This fragment was subcloned into the plasmid vector pUC18 using standard genetic engineering methodology, and then sequenced. This sequence showed very high homology to PRDC, indicating that this was indeed a fragment of human DCR5. Based on this information, exact primers corresponding to the 5' end and the 3' end of this sequence were engineered as shown below:

A. Sequence of fragment of human DCR5 generated by PCR is shown in SEQ ID NO: 5 (nucleotide sequence) and SEQ ID NO: 6 (amino acid sequence) in the attached sequence listing.

B. Sequence of primers synthesized based on the human DCR5 partial genomic sequence:

```
    (i) primer h/mDCR5.in1-5':
                                    SEQ ID NO: 7
    AGC CGC ACC ATC CTC AAC CGC TTC TGC TAC SEQ ID NO: 8
    Ser Arg Thr Ile Leu Asn Arg Phe Cys Tyr>

(ii) primer hDCR5.in2rev:
                                    SEQ ID NO: 9
    CTC GAG CTC CAC GAG GAC GGA GGT GAC SEQ ID NO: 10
    <Glu Leu Glu Val Leu Val Ser Thr Val
```

These primers were used in PCR to amplify a 140 bp fragment using liver cDNA as a template. To clone the full length hDCR5 ORF, we screened a Rapid Screen Human Liver cDNA Library Panel (OriGene Technologies, Inc.) by PCR using the above primers. This led to the identification of several independent cDNA clones. Sequencing of one of these clones revealed the existence of a 507 bp ORF that encodes for a 168 amino acid polypeptide which we have designated human DCR5. The sequence, which is set forth as SEQ ID NO: 11 (nucleotide) and SEQ ID NO: 12 (amino acid) in the attached sequence listing, has very high sequence identity (95%) to PRDC. In addition, it bears 65% sequence identity with human Gremlin, and 28 and 26% sequence identity with Cerberus and DAN, respectively, all of which are members of a family which comprise a conserved cysteine pattern and consensus sequence and all of which function as BMP antagonists. The human DCR5 DNA sequence set forth in SEQ ID NO: 11 is in the cloning vector pCMV6-XL3 (OriGene Technologies, Inc.), and is designated pCAE626.

Example 2

Construction and Expression of Human DCR5-myc3

The human DCR5 open reading frame (ORF) was amplified by PCR using two primers:

```
SEQ ID NO: 13: hDCR5 PCR5' (Eco) 5'-CAG ATA GAA
TTC GCC GCC ACC ATG GTG TGG AAG CTT TCC CTG TCC
TTG-3')

SEQ ID NO: 14: hDCR5 PCR3' (AgeI) (5'-CAC GAG ACC
GGT CTG CTT GTC CGA GTC GCT-3')
```

PCR amplification was performed using ExTaq DNA Polymerase (TaKaRa). The PCR product was purified away from excess primers, digested with the restriction endonucleases EcoRI and AgeI, gel-purified and subcloned into the mammalian expression vector pMT21-myc3 at the EcoRI and AgeI cloning sites, bringing the human DCR5 ORF (minus a stop codon) in frame with a triple myc-tag, the sequence of which is set forth below:

```
SEQ ID NO: 15: 5'-GAG CAG AAG CTG ATA TCC GAA GAA
GAC CTC GGC GGA GAG CAG AAG CTC ATA AGT GAG GAA
GAC TTG GGC GGA GAG CAG AAG CTT ATA TCC GAA GAA
GAT CTC GGA CCG TGA TAA-3'
```

This triple myc tag is contained in the vector immediately 3' to the unique AgeI site that was used for cloning purposes. The final DNA construct was verified by standard restriction analysis and dideoxy sequencing.

Human DCR5-myc3 protein was expressed in COS7 cells that were transiently transfected with the pMT21/human DCR5-myc3 DNA construct. The transfection was done using Lipofectamine (Life Technologies, Inc.) as described by the manufacturer. Serum-free conditioned media were collected two days after transfection and cleared of cell debris by low speed centrifugation. EDTA was added to the conditioned media to a concentration of 5 mM. The conditioned media were aliquoted and stored at −20° C. The expression of human DCR5-myc3 was verified by standard western blotting techniques using an anti-myc monoclonal antibody (9E10; 1 µg/ml) against the myc tag. Under standard non-reducing conditions, human DCR5-myc3 displayed an approximate molecular size of 30,000, which is consistent with the predicted molecular size of human DCR5-myc3 when accounting for glycosylation at the two potential N-linked glycosylation sites.

Example 3

Human DCR5 Binds to BMP2 and BMP4 But Not Other BMPs

Human DCR5-myc3 (1 ml of COS7 cell-derived serum-free conditioned media described supra) was co-incubated with human BMP-2 (1 µg/ml), or human BMP-4 (0.5 µg/1 ml) (R&D Systems), or human BMP-5 (1 g/ml) (R&D Systems), or mouse Nodal (also known as mBMP-16; provided as $^{35}$S-mouse Nodal expressed in X. laevis oocytes), or human BMP-11 (also known as human GDF-11; provided as $^{35}$S-human BMP-11 expressed in X. laevis oocytes), in the absence or in the presence of human noggin protein hNGΔB2 (described in published PCT application publication no. WO 99/03996, published Jan. 28, 1999, and incorporated in its entirety herein by reference), 2 to 5 µg/ml. The formation of a stable complex between human DCR5-myc3 and the different BMP family members was determined by immunoprecipitating human DCR5-myc3 and associated proteins using the anti-myc monoclonal antibody (9E10; 1 µg/ml) bound to Protein A Ultralink (Pierce). The binding reaction was carried out in the serum-free conditioned media containing 20 mM Tris pH 7.6, 150 mM NaCl, 0.1% Tween 20 (TBST), and 1 mg/ml bovine serum albumin (BSA). Binding was allowed to proceed for 1 hour at 25° C. in a reaction volume of 1.1 ml, with continuous mixing to keep the Protein A-Ultralink (Pierce) in suspension. Following incubation, the beads were pelleted by low speed centrifugation, washed once with TBST, transferred to fresh eppendorf tubes, and washed 3 additional times with TBST. Protein bound to the beads was solubilized by the addition of 25 µl of standard Laemli SDS-PAGE sample buffer and loaded onto 4 to 12% NuPAGE/MES gradient gels (Novex), which were run under standard reducing conditions. The electrophoresed proteins were subsequently transferred onto Immobilon P membranes and probed for the presence of human BMP-2 or human BMP-4 or human BMP-5 using antisera raised against each respective protein.

In one example, human DCR5-myc3 was shown to bind to human BMP-2. This interaction was blocked by the inclusion of 2 µg of hNGΔB2 in the binding reaction. This result indicates that the interaction between human BMP-2 and human DCR5-myc3 is specific. There was no binding of human BMP-2 to the beads when human DCR5-myc3 was not included in the binding reaction either in the presence or absense of hNGΔB2.

In another example, the ability of human DCR5-myc3 to bind to human BMP-4 was tested. Human DCR5-myc3 was able to bind human BMP-4. In addition, the interaction of human BMP-4 with human DCR5-myc3 was blocked by addition of hNGΔB2 (5 µg). As described above for human BMP-2, there was no binding of human BMP-4 to the beads when human DCR5-myc3 was omitted from the reaction mixture either in the presence or absence of hNGΔB2. Human DCR5 expressed in *E. Coli*, purified and refolded (see infra) was tested for its ability to compete with human DCR5-myc3 for binding to hBMP4. Inclusion of 5 µg of *E. coli*-expressed, purified and refolded human DCR-5 was able to block binding of human DCR5-myc3 to hBMP-4, indicating that this refolded human DCR-5 is active.

The ability of human DCR-5 to bind to other members of the BMP family was also tested. The results are as follows: hDCR-5 does not bind human BMP-5, mouse Nodal (mBMP-16), or human BMP-11 (also known as GDF-11). The lack of interaction with these BMPs provides further evidence that human DCR-5 is a specific antagonist of BMP-2 and BMP-4. However, the possibility that human DCR-5 binds to and blocks the activity of other BMP family members cannot be excluded.

Example 4

Construction of Human DCR5 *E. Coli* Expression Plasmid pRG764

A DNA fragment encoding the gene for human DCR5 was PCR amplified by standard techniques using the plasmid pCAE626 (described supra) as a template and the following oligonucleotides as amplification primers:

SEQ ID NO: 16: N1-hDCR5 (5'-<u>GAGAGACATGTCT</u>CGGAAGA
ACCGTCCGGCTGGCGCCTCCCCTCGCCTTAC-3')

SEQ ID NO: 17: C1-hDCR5 (5'<u>GAGAGCGGCCG</u>CTCATTACTG
CTTGTCCGAGTCGCTCAG-3').

The resulting 472 bp fragment includes nucleotides 64–504 of SEQ ID NO: 11 plus additional sequence for cloning (underlined in the oligonucleotide primer sequences supra) and encodes the mature human DCR5 gene starting with arginine at position 22 of SEQ ID NO: 12, which was determined by computer analysis to be the first amino acid after the signal sequence cleavage site. To facilitate cloning in *E. coli*, the human DCR5 encoding sequence was preceded by the codons for methionine and serine which introduced an Afl III restriction site for cloning. The codons for arginine and alanine at positions 25 and 27 in the human DCR5 sequence were changed from CGG and GCG to CGT and GCT, respectively, to reduce the GC content of the sequence proximal to the translation initiation site. These changes are silent mutations and do not alter the amino acid sequence. The resulting DNA fragment was digested with the restriction endonucleases Afl III, then ligated using standard techniques into the Nco1 and Eag1 cloning sites in the *E. coli* expression plasmid pRG663. The resulting plasmid, designated pRG764, contains the human DCR5 gene under transcriptional control of the T7 F1.1 promoter in a high copy number plasmid encoding the kanamycin resistance gene. The plasmid was confirmed by restriction enzyme analysis and DNA sequence determination using standard techniques known to skilled artisans.

Example 5

*E. Coli* Expression, Purification and Refolding of Human DCR5 Protein

Plasmid pRG764 (described supra) was transformed into the prototrophic *E. coli* K12 expression strain RFJ143 using standard transformation techniques. Strain RFJ143 expresses the phage T7 RNA polymerase under transcriptional control of the lacUV5 promoter. *E. coli* strain RFJ143 containing the pRG764 plasmid was grown in LB medium +20 µg/ml kanamycin. Expression of human DCR5 protein was induced by the addition of 1 mM IPTG. Induced cells were collected by centrifugation at 10,000 g for 10 minutes, resuspended in 10 volumes of 100 mM Tris-HCl, pH 8.5, 20 mM EDTA, and lysed by passage through a Niro-Soave Panda cell disrupter. The cell lysate was centrifuged at 10,000 g for 10 minutes and the pellet was resuspended in 10 volumes of 8 M guanindine-HCl, 50 mM Tris-HCl, pH 8.5, 1 mM EDTA, 100 mM $Na_2SO_3$, 10 mM $Na_2S_4O_6$ and stirred for 16 hours at room temperature. The solubilized inclusion bodies were fractionated on a Sephacryl S-300 column (Pharmacia) equilibrated in 8 M urea, 50 mM MES, pH 6.0, 200 mM NaCl, 1 mM EDTA. Fractions containing human DCR5 were pooled and diluted with 4 volumes of buffer containing 6 M urea, 20 mM MES, pH 6.0. The diluted human DCR5 pool was loaded onto an SP-Sepharose ion exchange column (Pharmacia) equilibrated with 6 M urea, 20 mM MES, pH 6.0 then eluted by a linear gradient ranging from 0 to 1 M NaCl in 6 M urea, 20 mM MES, pH 6.0. Fractions containing purified human DCR5 were pooled then diluted to about 0.1 mg/ml human DCR5 with 50 mM Tris-HCl, pH 8.5. Cysteine was added to 0.5 mM and NaCl was added to 1 M. This refold mix was incubated at 4° C. for 5 days with gentle stirring. Refolded human DCR5 was collected and purified by reversed-phase chromatography on a Phenomenex Jupiter C5 column run with a linear gradient from 0.1% TFA in $H_2O$ to 0.1% TFA in acetonitrile. Fractions containing refolded human DCR5 were pooled, dried under vacuum, and resuspended in PBS.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated human DCR5 protein, having the amino acid sequence as set forth in SEQ ID NO: 12.

2. A composition comprising the human DCR5 protein of claim 1, in a pharmaceutically acceptable carrier.

3. A human DCR5 protein produced by the method of:
   a) constructing a vector comprising a nucleic acid molecule containing a nucleotide sequence encoding human DCR5 protein as set forth in SEQ ID NO: 12, wherein the nucleic acid molecule is operatively linked to an expression control sequence capable of directing its expression in a host cell;
   b) introducing the vector of (a) into a host cell;
   c) growing the host cell of (b) under conditions which permit the production of human DCR5 protein; and
   d) recovering the human DCR5 protein so produced.

4. The protein of claim 3, wherein the host cell is a bacterial, yeast, insect or mammalian cell.

5. The human DCR5 protein of claim 1, fused to an immunoglobulin constant region.

6. The human DCR5 protein of claim 5, wherein the immunoglobulin constant region is the Fc portion of human IgG1.

* * * * *

SEQUENCE LISTING

<160> NUMBER OF SEQ ID NOS: 21

<210> SEQ ID NO 1
<211> LENGTH: 27
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 3, 12, 18
<223> OTHER INFORMATION: n = A, T, C or G

<400> SEQUENCE: 1
mgnaartayy tnaarwsnga ytggtgy                                              27

<210> SEQ ID NO 2
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 6, 9, 12, 21
<223> OTHER INFORMATION: n = A, T, C or G

<400> SEQUENCE: 2
caracngtnw sngargargg ntgy                                                 24

<210> SEQ ID NO 3
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 1, 4, 10, 13, 16
<223> OTHER INFORMATION: n = A, T, C or G

<400> SEQUENCE: 3
nggnggrtcn arnccnggrc a                                                    21

<210> SEQ ID NO 4
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 1, 7, 10, 19
<223> OTHER INFORMATION: n = A, T, C or G

<400> SEQUENCE: 4
narrttnacn swcatrcanc krca                                                 24

<210> SEQ ID NO 5
<211> LENGTH: 192
<212> TYPE: DNA
<213> ORGANISM: Homo sapien
<220> FEATURE:
<221> NAME/KEY: CDS
<222> LOCATION: (1)...(192)

<400> SEQUENCE: 5

```
cag aca gtg acg gag gag ggc tgc cgg agc cgc acc atc ctc aac cgc      48
Gln Thr Val Thr Glu Glu Gly Cys Arg Ser Arg Thr Ile Leu Asn Arg
 1               5                  10                  15 ttc tgc tac ggc cag tgc aac tcc ttc tac atc ccg cgg cac gtg aag      96
Phe Cys Tyr Gly Gln Cys Asn Ser Phe Tyr Ile Pro Arg His Val Lys
                20                  25                  30 aag gag gag gag tcc ttc cag tcc tgc gcc ttc tgc aag ccc cag cgc     144
Lys Glu Glu Glu Ser Phe Gln Ser Cys Ala Phe Cys Lys Pro Gln Arg
             35                  40                  45 gtc acc tcc gtc ctc gtg gag ctc gag tgc ccg gga cta gac ccc cca     192
Val Thr Ser Val Leu Val Glu Leu Glu Cys Pro Gly Leu Asp Pro Pro
 50                  55                  60
```

<210> SEQ ID NO 6
<211> LENGTH: 64
<212> TYPE: PRT
<213> ORGANISM: Homo sapien

<400> SEQUENCE: 6

```
Gln Thr Val Thr Glu Glu Gly Cys Arg Ser Arg Thr Ile Leu Asn Arg
 1               5                  10                  15

Phe Cys Tyr Gly Gln Cys Asn Ser Phe Tyr Ile Pro Arg His Val Lys
                20                  25                  30

Lys Glu Glu Glu Ser Phe Gln Ser Cys Ala Phe Cys Lys Pro Gln Arg
             35                  40                  45

Val Thr Ser Val Leu Val Glu Leu Glu Cys Pro Gly Leu Asp Pro Pro
 50                  55                  60
```

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
agccgcacca tcctcaaccg cttctgctac                                     30

<210> SEQ ID NO 8
<211> LENGTH: 10
<212> TYPE: PRT
<213> ORGANISM: Artificial Sequence
<220> FEATURE:
<223> OTHER INFORMATION: Synthetic Construct

<400> SEQUENCE: 8

```
Ser Arg Thr Ile Leu Asn Arg Phe Cys Tyr
 1               5                  10
```

<210> SEQ ID NO 9
<211> LENGTH: 27
<212> TYPE: DNA
<213> ORGANISM: Artificial Sequence
<220> FEATURE:
<223> OTHER INFORMATION: Primer

<400> SEQUENCE: 9
ctcgagctcc acgaggacgg aggtgac                                        27

<210> SEQ ID NO 10
<211> LENGTH: 9
<212> TYPE: PRT
<213> ORGANISM: Artificial Sequence
<220> FEATURE:

<223> OTHER INFORMATION: Synthetic Construct

<400> SEQUENCE: 10

Glu Leu Glu Val Leu Val Ser Thr Val
 1               5

<210> SEQ ID NO 11
<211> LENGTH: 507
<212> TYPE: DNA
<213> ORGANISM: Homo sapien
<220> FEATURE:
<221> NAME/KEY: CDS
<222> LOCATION: (1)...(504)

<400> SEQUENCE: 11

| atg ttc tgg aag ctt tcc ctg tcc ttg ttc ctg gtg gcg gtg ctg gtg | 48 |
| Met Phe Trp Lys Leu Ser Leu Ser Leu Phe Leu Val Ala Val Leu Val | |
|  1               5                  10                  15 | |

| aag gtg gcg gaa gcc cgg aag aac cgg ccg gcg ggc gcc atc ccc tcg | 96 |
| Lys Val Ala Glu Ala Arg Lys Asn Arg Pro Ala Gly Ala Ile Pro Ser | |
|                 20                  25                  30 | |

| cct tac aag gac ggc agc agc aac aac tcg gag aga tgg cag cac cag | 144 |
| Pro Tyr Lys Asp Gly Ser Ser Asn Asn Ser Glu Arg Trp Gln His Gln | |
|             35                  40                  45 | |

| atc aag gag gtg ctg gcc tcc agc cag gag gcc ctg gtg gtc acc gag | 192 |
| Ile Lys Glu Val Leu Ala Ser Ser Gln Glu Ala Leu Val Val Thr Glu | |
|         50                  55                  60 | |

| cgc aag tac ctc aag agt gac tgg tgc aag acg cag ccg ctg cgg cag | 240 |
| Arg Lys Tyr Leu Lys Ser Asp Trp Cys Lys Thr Gln Pro Leu Arg Gln | |
|  65                  70                  75                  80 | |

| acg gtg agc gag gag ggc tgc cgg agc cgc acc atc ctc aac cgc ttc | 288 |
| Thr Val Ser Glu Glu Gly Cys Arg Ser Arg Thr Ile Leu Asn Arg Phe | |
|                 85                  90                  95 | |

| tgc tac ggc cag tgc aac tcc ttc tac atc ccg cgg cac gtg aag aag | 336 |
| Cys Tyr Gly Gln Cys Asn Ser Phe Tyr Ile Pro Arg His Val Lys Lys | |
|            100                 105                 110 | |

| gag gag gag tcc ttc cag tcc tgc gcc ttc tgc aag ccc cag cgc gtc | 384 |
| Glu Glu Glu Ser Phe Gln Ser Cys Ala Phe Cys Lys Pro Gln Arg Val | |
|        115                 120                 125 | |

| acc tcc gtc ctc gtg gag ctc gag tgc ccc ggc ctg gac cca ccc ttc | 432 |
| Thr Ser Val Leu Val Glu Leu Glu Cys Pro Gly Leu Asp Pro Pro Phe | |
|    130                 135                 140 | |

| cga ctc aag aaa atc cag aag gtg aag cag tgc cgg tgc atg tcc gtg | 480 |
| Arg Leu Lys Lys Ile Gln Lys Val Lys Gln Cys Arg Cys Met Ser Val | |
| 145                 150                 155                 160 | |

| aac ctg agc gac tcg gac aag cag tga | 507 |
| Asn Leu Ser Asp Ser Asp Lys Gln | |
|                 165 | |

<210> SEQ ID NO 12
<211> LENGTH: 168
<212> TYPE: PRT
<213> ORGANISM: Homo sapien

<400> SEQUENCE: 12

Met Phe Trp Lys Leu Ser Leu Ser Leu Phe Leu Val Ala Val Leu Val
 1               5                  10                  15

Lys Val Ala Glu Ala Arg Lys Asn Arg Pro Ala Gly Ala Ile Pro Ser
                20                  25                  30

Pro Tyr Lys Asp Gly Ser Ser Asn Asn Ser Glu Arg Trp Gln His Gln
            35                  40                  45

-continued

```
Ile Lys Glu Val Leu Ala Ser Ser Gln Glu Ala Leu Val Val Thr Glu
 50                  55                  60
Arg Lys Tyr Leu Lys Ser Asp Trp Cys Lys Thr Gln Pro Leu Arg Gln
 65                  70                  75                  80
Thr Val Ser Glu Glu Gly Cys Arg Ser Arg Thr Ile Leu Asn Arg Phe
                 85                  90                  95
Cys Tyr Gly Gln Cys Asn Ser Phe Tyr Ile Pro Arg His Val Lys Lys
            100                 105                 110
Glu Glu Glu Ser Phe Gln Ser Cys Ala Phe Cys Lys Pro Gln Arg Val
            115                 120                 125
Thr Ser Val Leu Val Glu Leu Glu Cys Pro Gly Leu Asp Pro Pro Phe
130                 135                 140
Arg Leu Lys Lys Ile Gln Lys Val Lys Gln Cys Arg Cys Met Ser Val
145                 150                 155                 160
Asn Leu Ser Asp Ser Asp Lys Gln
                165
```

<210> SEQ ID NO 13
<211> LENGTH: 48
<212> TYPE: DNA
<213> ORGANISM: Artificial Sequence
<220> FEATURE:
<223> OTHER INFORMATION: Primer

<400> SEQUENCE: 13
cagatagaat tcgccgccac catggtgtgg aagctttccc tgtccttg           48

<210> SEQ ID NO 14
<211> LENGTH: 30
<212> TYPE: DNA
<213> ORGANISM: Artificial Sequence
<220> FEATURE:
<223> OTHER INFORMATION: Primer

<400> SEQUENCE: 14
cacgagaccg gtctgcttgt ccgagtcgct                               30

<210> SEQ ID NO 15
<211> LENGTH: 114
<212> TYPE: DNA
<213> ORGANISM: Artificial Sequence
<220> FEATURE:
<223> OTHER INFORMATION: Triple myc tag

<400> SEQUENCE: 15
gagcagaagc tgatatccga agaagacctc ggcggagagc agaagctcat aagtgaggaa      60
gacttgggcg agagcagaa gcttatatcc gaagaagatc tcggaccgtg ataa           114

<210> SEQ ID NO 16
<211> LENGTH: 52
<212> TYPE: DNA
<213> ORGANISM: Artificial Sequence
<220> FEATURE:
<223> OTHER INFORMATION: Primer

<400> SEQUENCE: 16
gagagacatg tctcggaaga accgtccggc tggcgccatc ccctcgcctt ac             52

<210> SEQ ID NO 17
<211> LENGTH: 39
<212> TYPE: DNA
<213> ORGANISM: Artificial Sequence

```
-continued

<220> FEATURE:
<223> OTHER INFORMATION: Primer

<400> SEQUENCE: 17
gagagcggcc gctcattact gcttgtccga gtcgctcag                    39

<210> SEQ ID NO 18
<211> LENGTH: 9
<212> TYPE: PRT
<213> ORGANISM: Artificial Sequence
<220> FEATURE:
<223> OTHER INFORMATION: Mammalian

<400> SEQUENCE: 18

Arg Lys Tyr Leu Lys Ser Asp Trp Cys
1               5

<210> SEQ ID NO 19
<211> LENGTH: 8
<212> TYPE: PRT
<213> ORGANISM: Artificial Sequence
<220> FEATURE:
<223> OTHER INFORMATION: Mammalian

<400> SEQUENCE: 19

Gln Thr Val Ser Glu Glu Gly Cys
1               5

<210> SEQ ID NO 20
<211> LENGTH: 7
<212> TYPE: PRT
<213> ORGANISM: Artificial Sequence
<220> FEATURE:
<223> OTHER INFORMATION: Mammalian

<400> SEQUENCE: 20

Pro Pro Asp Leu Gly Pro Cys
1               5

<210> SEQ ID NO 21
<211> LENGTH: 8
<212> TYPE: PRT
<213> ORGANISM: Artificial Sequence
<220> FEATURE:
<223> OTHER INFORMATION: Mammalian

<400> SEQUENCE: 21

Leu Asn Val Ser Met Cys Arg Cys
1               5
```